(12) United States Patent
Garell et al.

(10) Patent No.: US 7,774,053 B2
(45) Date of Patent: Aug. 10, 2010

(54) NEURAL PROBE ARRAY

(75) Inventors: P. Charles Garell, Madison, WI (US);
Justin C. Williams, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 175 days.

(21) Appl. No.: 11/095,363

(22) Filed: Mar. 31, 2005

(65) Prior Publication Data

US 2006/0224060 A1    Oct. 5, 2006

(51) Int. Cl.
*A61B 5/04* (2006.01)
*A61B 5/05* (2006.01)

(52) U.S. Cl. .................. 600/544; 600/545; 600/546; 600/554; 600/372; 600/373; 600/378; 600/382; 600/383

(58) Field of Classification Search ........... 600/544, 600/545, 546, 554, 372, 373, 378, 382, 383
See application file for complete search history.

(56) References Cited

U.S. PATENT DOCUMENTS 6,171,239 B1 * 1/2001 Humphrey .......... 600/372
6,324,429 B1 * 11/2001 Shire et al. .......... 607/54
6,330,466 B1   12/2001 Hofmann et al. .......... 600/378
2003/0100823 A1 * 5/2003 Kipke et al. .......... 600/378
2004/0054276 A1 * 3/2004 Finneran et al. .......... 600/393

OTHER PUBLICATIONS

"3-D Silicon Probe Array With Hybrid Polymer Interconnect for Chronic Cortical Recording," Proceedings of the 1st International IEEE EMS, Conference of Neural Engineering, Capri Island, Italy, Mar. 20-22, 2003, pp. 181-184, by J. F. Hetke, J. C. Williams, D. S. Pellinen, R. J. Vetter and D.R. Kipke.
"Flexible Polyimide-Based Intracortical Electrode Arrays With Bioactive Capability," IEEE Transactions on Biomedical Engineering, vol. 48, No. 3, Mar. 2001, by Patrick J. Rousche, David S. Pellinen, David P. Pivin, Jr., Justin C. Williams, Rio J. Vetter and Daryl R. Kipke.

* cited by examiner

*Primary Examiner*—Max Hindenburg
*Assistant Examiner*—Jeffrey G Hoekstra
(74) *Attorney, Agent, or Firm*—Boyle Fredrickson, S.C.

(57) ABSTRACT

A neural probe array is provided for subdural implantation to record intracranial field potentials in the brain. The neural probe array includes a base having first and second sides and a plurality of apertures therebetween. A plurality of contacts are spaced along the first side of the base for recording the field potentials. It is contemplated to provide drug delivery through the apertures in the base in order to enhance the biocompatibility of the neural probe array and to utilize the field potentials recorded by the contacts to drive an external device.

19 Claims, 3 Drawing Sheets

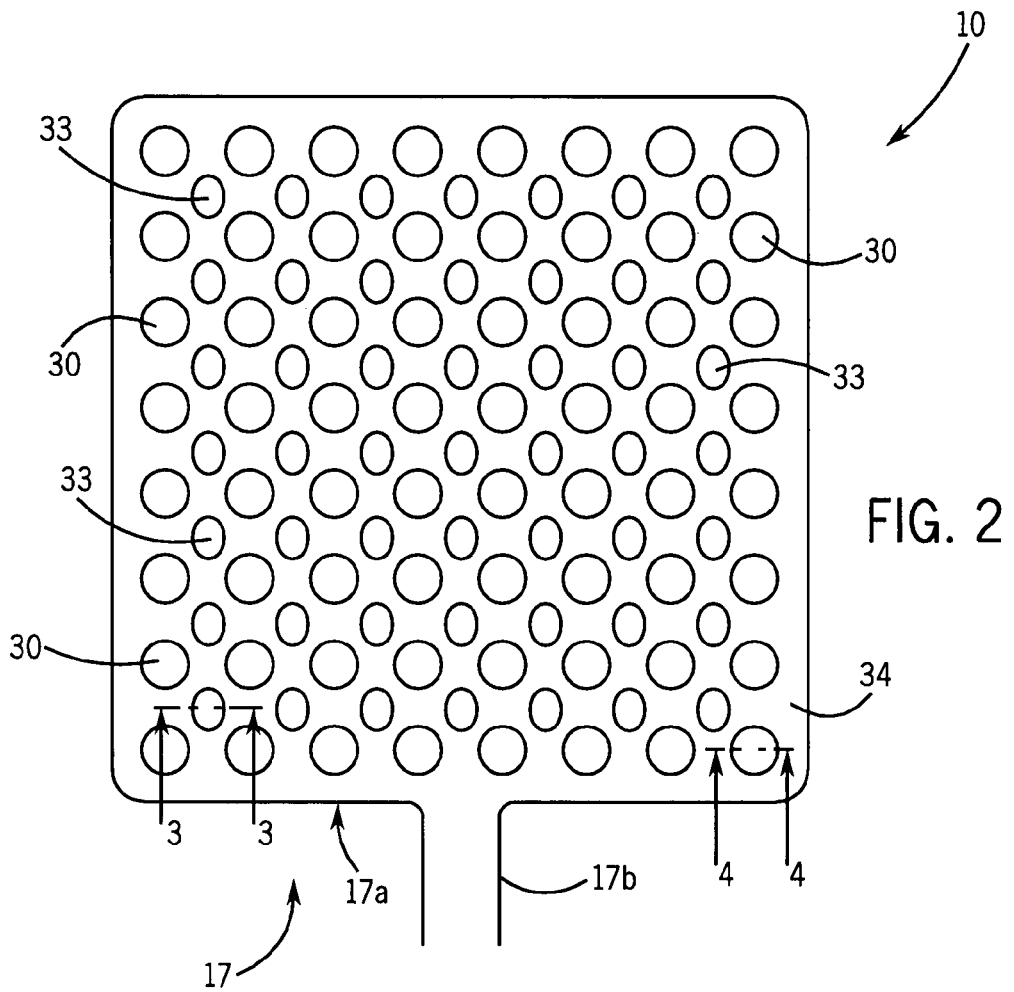
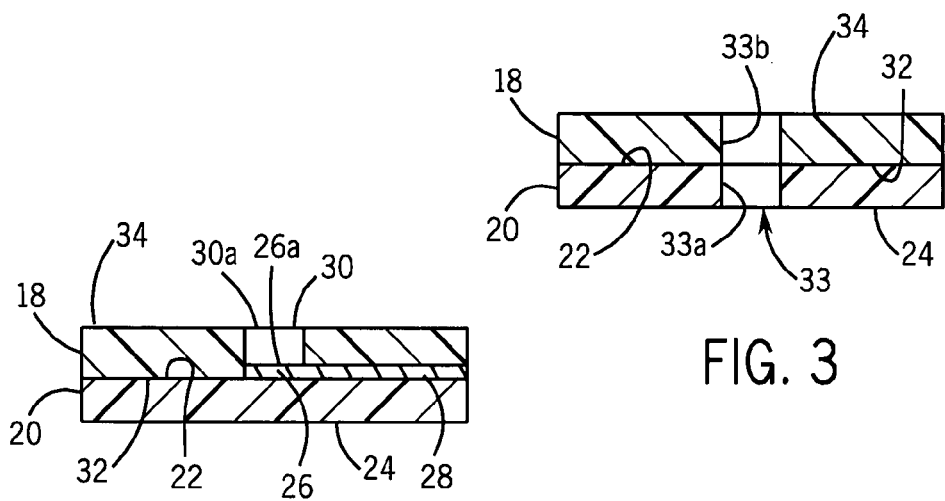

NEURAL PROBE ARRAY

REFERENCE TO GOVERNMENT GRANT

This invention was made with United States government support awarded by the following agencies: NIH DC006415. The United States has certain rights in this invention.

FIELD OF THE INVENTION

This invention relates generally to neural probe arrays, and in particular, to a neural probe array for subdural implantation by neuro surgeons to record intracranial field potentials in animal or human brains.

BACKGROUND AND SUMMARY OF THE INVENTION

As is known, electrodes have been used to monitor and record neural activity. For example, these electrodes may take the form of a stiff and sharpened insulated metallic wire, or a drawn glass pipette filled with an aqueous conductor. The electrode or an array of electrodes is inserted through the pia or the dura and positioned in the target neurons in the brain to record neural activity. While functional for their intended purpose, these prior electrodes have certain limitations. By way of example, over time, the brain may respond to exposure to the electrode by electrically insulating the device. Further, there may be a loss of neural activity do to neuronal death around the device. Hence, the devices may not remain functional for extended periods of time.

It can be appreciated that the development of a neural interface that provides reliable and stable long-term implant function could be used in a wide variety of applications. For example, in cases of spinal cord injury, the brain of the individual may still function to generate motor signals that would normally be conveyed to the muscles. As such, it is contemplated to monitor these motor signals within the brain of a paralyzed individual and transmit such signals to an extension device that drives an individual's muscles or an extracorporeal device and bypass the injured spinal cord. However, in order to continually monitor localized brain activity, the development of a neural interface that provides reliable and stable long term implant functionality is necessary.

A neural interface device that is intended for successful long-term implantation in the nervous system must meet a strict series of criteria in the electrical, mechanical, and biological arenas. Electrically, the devices must maintain its appropriate insulating and conductive properties over extended implant durations in an intracranial environment. Mechanically, the device must be capable of withstanding any possible micro motion with the brain tissue during implantation. Biologically, the device must maintain a biocompatible profile that does not induce an excessive foreign body or immune response.

Therefore, it is a primary object and feature of the present invention to provide a neural probe array for subdural implantation that records intracranial field potentials in a brain.

It is a still further object and feature of the present invention to provide a neural probe array for subdural implantation that is more biocompatible than prior intracortical neural interfaces.

It is a still further object and feature of the present invention to provide a neural probe array for subdural implantation that is simple and inexpensive to manufacture.

It is a still further object and feature of the present invention to provide a neural probe array for subdural implantation that can be implanted in patients for a considerably longer period of time than conventional electrodes.

In accordance with the present invention, a neural probe array is provided for subdural implantation. It is intended that the neural probe array record intracranial field potentials in a brain. The neural probe array includes a base having first and second sides and a plurality of apertures extending therebetween. A plurality of contacts are spaced along the first side of the base for recording the field potentials.

The base includes a first layer having a first outer surface defining the first side of the base and a second inner surface. The base also includes a second layer having a first outer surface defining a second side of the base and a second inner surface bonded to the inner surface of the first layer. It is contemplated for the first and second layers to be formed from insulators. A plurality of conductors are disposed between the first and second layers of the base. Each conductor has a first end operatively connected to a corresponding one of the plurality of contacts and a second opposite end operatively connected to a connector spaced from the base.

The plurality of apertures through the base may be arranged in rows and columns. Similarly, the plurality of contacts on the first side of the base may be arranged in rows and columns. Each of the plurality of contacts has a diameter in the range of 200 microns to 2 millimeters. Further, each of the plurality of contacts is spaced from an adjacent contact by a minimum distance of 300 microns.

In accordance with a further aspect of the present invention, a neural probe array is provided for subdural implantation. It is intended for the neural probe array to record field potentials in a brain. The neural probe array includes a porous base having first and second sides. A plurality of contacts are spaced along the first side of the base for recording the field potentials.

The base includes a plurality of apertures therethrough. The apertures are arranged in rows and columns. Similarly, the plurality of contacts along the first side of the base may be arranged in rows and columns. The neural probe array may also include a plurality of conductors. Each conductor has a first end operatively connected to the corresponding one of the plurality of contacts and a second opposite end operatively connected to a connector spaced from the base. A portion of each of the plurality of contactors is disposed within the base.

In accordance with a further aspect of the present invention, a neural probe array is provided for subdural implantation. It is intended for the neural probe array to record intracranial field potentials in a brain. The neural probe array includes a first layer having a first outer surface and a first inner surface and a plurality of apertures therethrough. The neural probe array further includes a second layer having a second outer surface, a second inner surface bonded to the first inner surface of the first layer, and a plurality of apertures therethrough. The plurality of apertures through the second layer are axially aligned with the plurality of apertures in the first layer. A plurality of contacts are spaced along the first outer surface of the first layer for recording the field potentials. A plurality of conductors are also provided. Each conductor has at least a portion disposed between the first and second layers, a first end operatively connected to a corresponding one of the plurality of contacts, and a second opposite end.

The plurality of contacts of the neural probe array may be arranged in rows and columns along the outer surface of the first layer. Each of the plurality of contacts has a diameter in a range of 200 microns to 2 millimeters and is spaced from an adjacent contact by a minimum distance of 300 microns. It is also contemplated to arrange the plurality of apertures through the first layer in rows and columns.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings:

FIG. 2 is a top plan view of the neural probe array of the present invention;

FIG. 3 is a cross-sectional view of the neural probe array of the present invention taken along line 3-3 of FIG. 2;

FIG. 4 is a cross-sectional view of the neural probe array of the present invention taken along line 4-4 of FIG. 2.

DETAILED DESCRIPTION OF THE DRAWINGS

Figure 1:
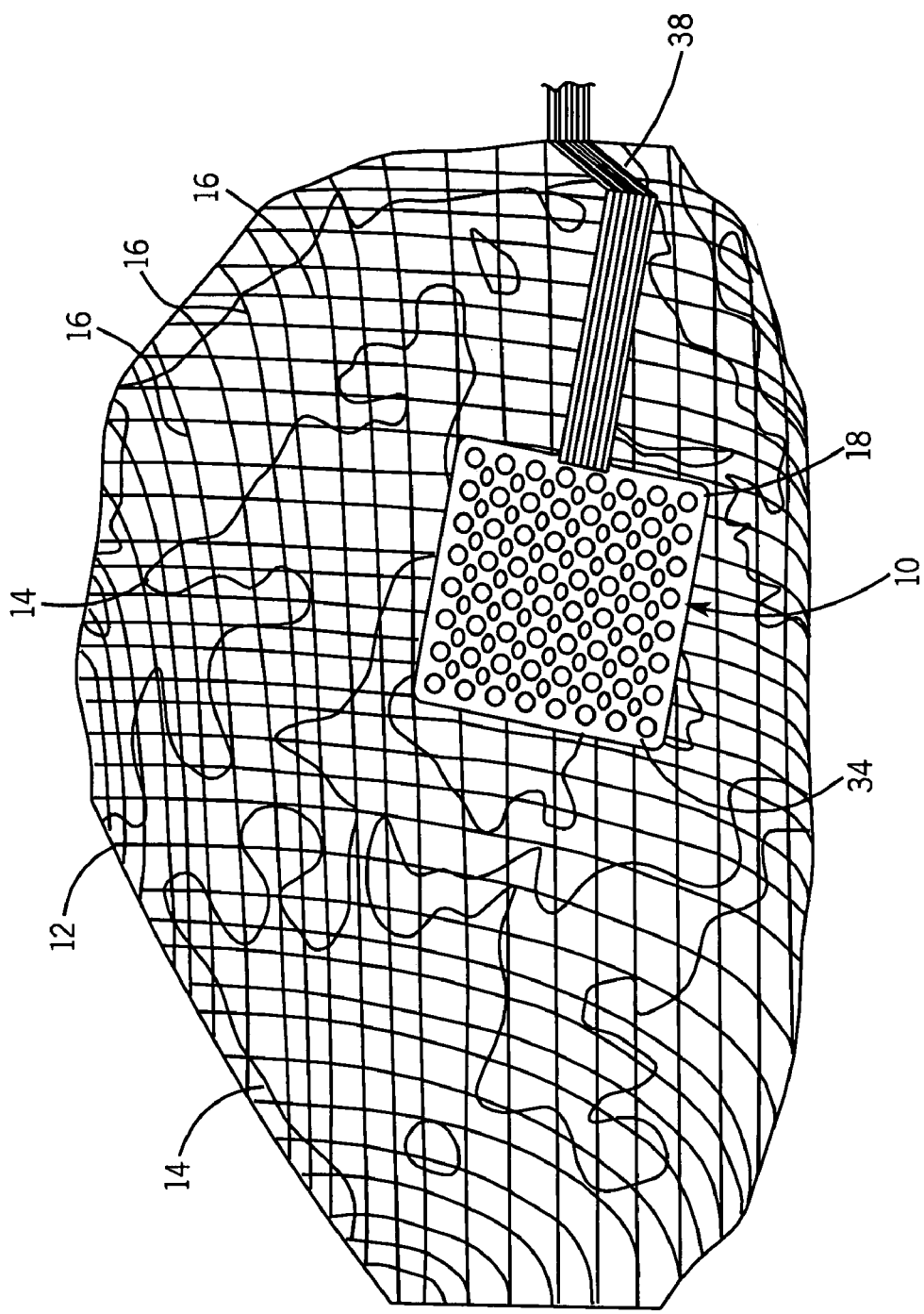
FIG. 1 is a schematic view of a neural probe array in accordance with the present invention implanted within the cranium of an individual.

Referring to FIG. 1, a neural probe array in accordance with the present invention is generally designated by the reference numeral 10. It is intended that neural probe array 10 be implanted on surface 12 of brain 14 within a cranium 16, depicted as a grid pattern of intersecting lines in FIG. 1. It can be appreciated that neural probe array 10 may be implanted within cranium 16 of an animal or a human without deviating from the scope of the present invention.

Referring to FIGS. 2-4, neural probe array 10 includes pad 17 defined by a generally square contact portion 17a and neck portion 17b extending from a first side of contact portion 17a of pad 17. Pad 17 further includes first and second layers 18 and 20, respectively, formed from biocompatible polymers that provide maximum flexibility. The flexibility of each layer 18 and 20 is intended to provide stronger relief against the forces of micro motion between the tissue of the brain 14 and neural probe array 10. By way of example, first and second layers 18 and 20, respectively, are fabricated from a photosensitive polymer, as hereinafter described, to facilitate the manufacture of neural probe array 10. It is contemplated that the surface chemistry of pad 17 allows for a host of bioactive organic species to be either absorbed or covelantly bonded to the surfaces thereof. The flexibility and bioactivity of pad 17 are intended to provide an optimal implant environment and extend the time period that neural probe array 10 may be maintained within cranium 16 without inducing excessive foreign body or immune response.

It can be appreciated that neural probe array 10 may be constructed in a variety of manners. By way of example, in order to construct neural probe array 10, it is contemplated to provide a layer polymerizable material, such as a negative photoactive polyimide, of predetermined dimensions and to polymerize the same using the standard photolithography techniques. By exposing the layer of polymerizable material to a polymerizing agent such as ultraviolet light, the layer of polymerizable material solidifies and forms the second layer 20. By way of example, second layer 20 has a configuration corresponding to the configuration of pad 17. Further, it is contemplated to provide apertures 33a through second layer 20 arranged in rows and columns, for reasons hereinafter described.

After polymerization, second layer 20 is partially cured for a predetermined time period at a predetermined temperature (e.g., 15 minutes at 350° C.) in a nitrogen purged oven to protect the developed pattern from subsequent processing steps and to provide a suitable surface for metal deposition. As fabricated, second layer 20 includes inner surface 22 and outer surface 24. A reactive ion etch is used to micro-roughen inner surface 28 of second layer 20 prior to depositing a metal layer thereon. A thin layer of chromium (e.g. 250 Å) is then electron-beam evaporated on inner surface 22 of second layer 20 as an inter-metallic adhesion promoter and a layer of an earth metal such as gold, platinum or iridium of a predetermined thickness (e.g., 200 nm) is evaporated onto inner surface 22 of layer 20. A positive photoresist is patterned over the layer of earth metal to delineate contact pads 26 and wire traces 28. The excess earth metal is etched from inner surface 22 of second layer 20 leaving contact pads 26 and wire traces 28 deposited thereon. Preferably, contact pads 26 are arranged in rows and columns on upper surface 22 of second layer 20. Each wire trace 28 has a first end integral with a corresponding contact pad and a second end extending along neck portion 17b of pad 17.

Figure 5:
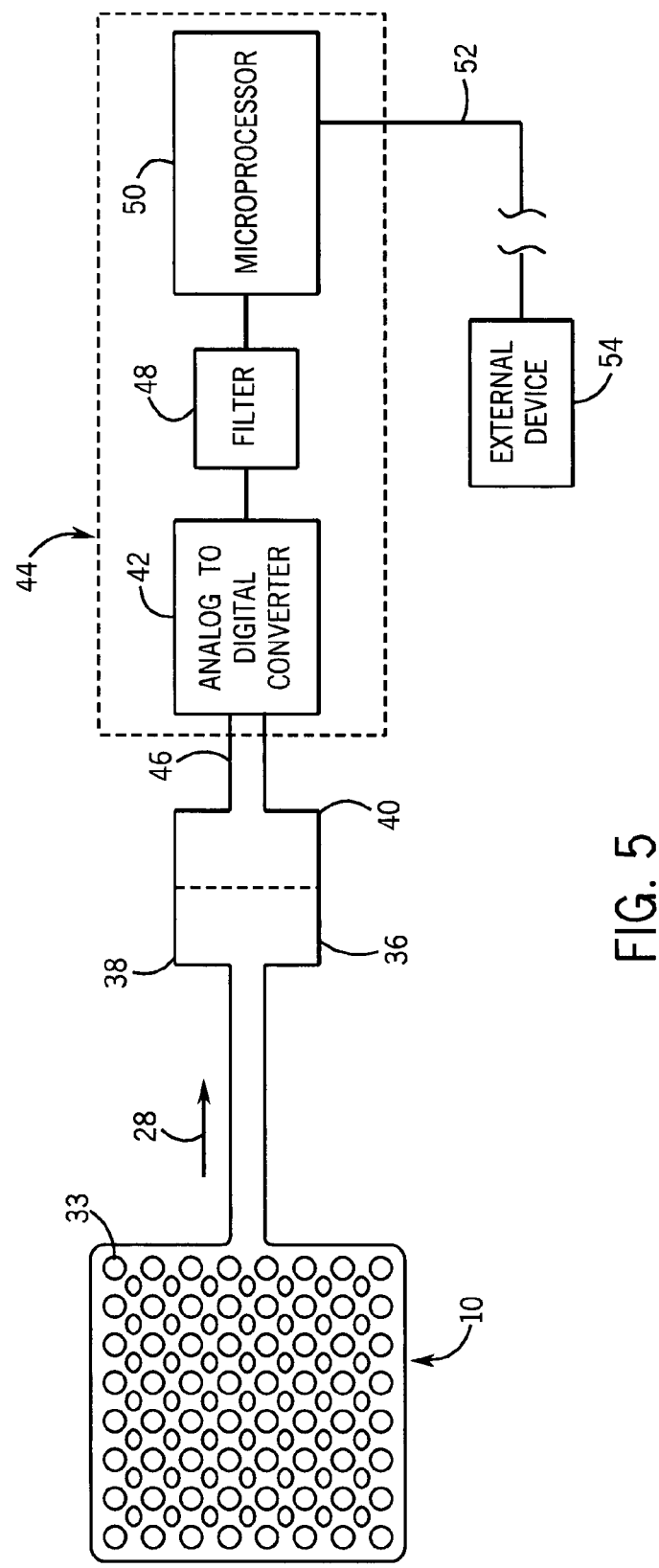
FIG. 5 is a schematic view of a neural interface system incorporating the neural probe array of the present invention

A reactive ion etch is used to clean and micro-roughen the exposed inner surface 22 of second layer 20 and the exposed surfaces of contact pads 26 and wire traces 28 prior to the application of first layer 18 of a photoactive polyimide thereon. The photoactive polyimide deposited on inner surface 22 of second layer 20 is spun to the same thickness as second layer 20. Thereafter, first layer 18 is polymerized and developed using standard photolithography techniques to encapsulate wire traces 28 and reveal upper surface 26a of contact pad 26. In addition, apertures 33b, axially aligned with corresponding apertures 33a in second layer 20, are formed in first layer 18, for reasons hereinafter described. Once first layer 18 is polymerized, contacts 30 are deposited onto contact pads 26 and first layer 18 is cured so as to bond inner surface 32 of first layer 18 to inner surface 24 of second layer 20. It is intended that terminal ends 30a of contacts 30 be generally co-planar with outer surface 34 of first layer 18; that apertures 33a through second layer 20 be axially aligned with apertures 33b through first layer 18 so as to define apertures 33 through pad 17; and that contacts 30 be arranged in rows and columns along outer surface 34 of first layer 18, FIGS. 2 and 5. In addition, apertures 33 are arranged in rows and columns in contact portion 17a of pad 17. Referring to FIG. 5, wire traces 28 are electrically coupled to contacts 30 through corresponding contact pads 26 and include second opposite ends electrically coupled to first portion 36 of electrical connector 38.

In operation, neural probe array is implanted in cranium 16 of an individual such that terminal ends 30a of contacts 30 are positioned adjacent target neurons in the brain. Apertures 33 through contact portion 17a of pad 17 make neural probe array 10 porous, and as such, increase the biocompatibility between neural probe array 10 and brain 14. Further, it is contemplated to provide chemicals, drugs or other stimuli within apertures 33 of neural probe array 10 to further enhance the biocompatibility of neural probe array 10 and brain 14 or to treat various neurological disorders. Thereafter, first portion of electrical connector 38 is bonded to cranium 16 of an individual.

In order to monitor the inner cranial field potentials associated with the target neurons in the brain, first portion 36 of electrical connector 38 is electrically coupled to a second portion 40 of connector 38, that is, in turn, electrically coupled to an analog-to-digital converter 42 of signal processing unit 44 by line 46. Analog-to-digital converter 42 of signal processing unit 44 receives the analog signals corresponding to the intracranial field potentials of the target neurons detected by contacts 30 and converts such signals to a digital format. The digital signals are transmitted to and filtered by filter 48 and provided to microprocessor 50 within signal processing unit 44. Microprocessor 50 executes a predetermined algorithm so as to generate instructions on line 52 for an external device 54. External device 54 may take the form of a mechanical drive system that drives the muscles of a user in response to the intracranial field potentials detected by contacts 30 of neural probe array 10. Alternatively, external device 54 may take the form of a prosthesis or a monitor for detecting abnormal electrical activity within the brain (e.g. seizures).

As described, the neural probe array of the present invention is less invasive compared to conventional electrodes from surgical prospective. More specifically, neural probe array 10 of the present invention is more flexible; has a better signal to noise ratio; and is more biocompatible then conventional electrodes. As a result, neural probe array 10 of the present invention is more adapted for chronic use and can be implanted in patients for a considerably longer period of time than conventional electrodes. Further, due to the photolithographic fabrication techniques, the manufacturing costs associated with the neural probe array of the present invention is significantly lower than the manufacturing costs associated with prior conventional electrodes.

Various modes of carrying out the invention are contemplated as being within the scope of the following claims particularly pointing out and distinctly claiming the subject matter, which is regarded as the invention.

We claim:

1. A neural probe array for subdural implantation to record intracranial field potentials in a brain, comprising:
    a base having first and second sides and a plurality of apertures extending therebetween, each aperture extending along a corresponding axis and having a first end communicating with the first side of the base and a second end communicating with a second side of the base;
    a plurality of contacts laterally spaced from each axis along which the plurality of apertures extend and being positioned along the first side of the base for recording the field potentials, the contacts:
        having terminal ends co-planar with the first side of the base so as to allow the terminal ends of the contacts to be positioned adjacent target neurons in the brain; and
        being arranged in a generally rectangular pattern for engagement with the brain; and
    a plurality of conductors, each conductor having a first end operatively connected to a corresponding one of the plurality of contacts and a second opposite end;
    wherein:
        the first side of the base is in fluid communication with the second side of the base via the plurality of apertures; and
        the base is free of active electronic components mounted thereto.

2. The neural probe array of claim 1 wherein the base includes:
    a first layer having a first outer surface defining the first side of the base and a second inner surface; and
    a second layer having a first outer surface defining the second side of the base and a second inner surface bonded to the inner surface of the first layer.

3. The neural probe array of claim 1 wherein the first and second layers are formed from insulators.

4. The neural probe array of claim 1 wherein the second ends of the plurality of conductors are operatively connected to a connector spaced from the base.

5. The neural probe array of claim 1 wherein a portion of each of the plurality of conductors is positioned between the first and second layers of the base.

6. The neural probe array of claim 1 wherein the plurality of apertures through the base are arranged in rows and columns.

7. The neural probe array of claim 1 wherein the plurality of contacts along the first side of the base are arranged in rows and columns.

8. The neural probe array of claim 1 wherein each of the plurality of contacts has a diameter in the range of 200 microns to 2 millimeters.

9. The neural probe array of claim 1 wherein each of the plurality of contacts is spaced from an adjacent contact by a minimum distance of 300 microns.

10. A neural probe array for subdural implantation to record field potentials in a brain, comprising:
    a porous base having first and second sides, the base being free of active electronic components mounted thereto;
    a plurality of contacts spaced along the first side of the base for recording the field potentials, the plurality of contacts having terminal ends co-planar with the first side of the base so as to allow the terminal ends of the contacts to be positioned adjacent target neurons in the brain;
    a plurality of conductors, each conductor having a first end operatively connected to a corresponding one of the plurality of contacts and a second opposite end; and
    a connector operatively connected to the second ends of the conductors at a location spaced from the base, the connector being connectable to a signal processing unit;
    wherein:
        the recorded field potentials are transmitted from the first ends of the plurality of conductors to the second ends of the conductors; and
        the base includes a plurality of apertures therethrough, the apertures arranged in rows and columns;
        each aperture extending along a corresponding axis and having a first end communicating with the first side of the base and a second end communicating with a second side of the base such that the first side of the base is in fluid communication with the second side of the base via the plurality of apertures; and
        each of the contacts being laterally spaced from the axes of the apertures.

11. The neural probe array of claim 10 wherein the plurality of contacts are arranged in rows and columns along the first side of the base.

12. The neural probe array of claim 10 wherein a portion of each of the plurality of conductors is disposed within the base.

13. The neural probe array of claim 10 wherein each of the plurality of contacts has a diameter in the range of 200 microns to 2 millimeters.

14. The neural probe array of claim 10 wherein each of the plurality of contacts is spaced from an adjacent contact by a minimum distance of 300 microns.

15. A neural probe array for subdural implantation to record intracranial field potentials in a brain, comprising:
    a first layer having a first outer surface, a first inner surface and a plurality of apertures therethrough;
    a second layer having a second outer surface, a second inner surface bonded to the first inner surface of the first layer, and a plurality of apertures therethrough, the plurality of apertures through the second layer being axially aligned with the plurality of apertures through the first layer so as to define a plurality of holes;

a plurality of contacts spaced along the first outer surface of the first layer for recording the field potentials, the plurality of contacts having terminal ends co-planar with the first outer surface of the first layer so as to allow the terminal ends of the contacts to be positioned adjacent target neurons in the brain; and a plurality of conductors, each conductor having:
- at least a portion disposed between the first and second layers;
- a first end operatively connected to a corresponding one of the plurality of contacts; and
- a second opposite end;

wherein:
- the plurality of holes in the first and second layers are arranged in rows and columns and extend along corresponding axes;
- each of the plurality of contacts is laterally spaced from the axes of the plurality of holes;
- the first outer surface of the first layer is in fluid communication with the second outer surface of the second layer via the plurality of holes;
- each hole is generally equally spaced from an adjacent hole in the row and column; and
- the first and second layers are free of active electronic components.

16. The neural probe array of claim 15 wherein the plurality of contacts are arranged in rows and columns along the first outer surface of the first layer.

17. The neural probe array of claim 15 further comprising a connector operatively connected to the second ends of the conductor for coupling the plurality of conductors to a signal processor.

18. The neural probe array of claim 15 wherein each of the plurality of contacts has a diameter in the range of 200 microns to 2 millimeters.

19. The neural probe array of claim 15 wherein each of the plurality of contacts is spaced from an adjacent contact by a minimum distance of 300 microns.

* * * * *